(12) United States Patent
Xu et al.

(10) Patent No.: US 10,004,224 B2
(45) Date of Patent: Jun. 26, 2018

(54) METHOD FOR PRODUCING AQUEOUS SUSPENSION CONCENTRATE FORMULATIONS

(71) Applicant: BASF SE, Ludwigshafen (DE)

(72) Inventors: Wen Xu, Cary, NC (US); Ralph Paulini, Cary, NC (US); Michael Krapp, Altrip (DE); Kara Benton, Morrisville, NC (US)

(73) Assignee: BASE SE, Ludwigshafen (DE)

( * ) Notice: Subject to any disclaimer, the term of this patent is extended or adjusted under 35 U.S.C. 154(b) by 363 days.

(21) Appl. No.: 14/762,996

(22) PCT Filed: Jan. 24, 2014

(86) PCT No.: PCT/EP2014/051377
§ 371 (c)(1),
(2) Date: Jul. 23, 2015

(87) PCT Pub. No.: WO2014/114738
PCT Pub. Date: Jul. 31, 2014

(65) Prior Publication Data
US 2015/0366184 A1    Dec. 24, 2015

Related U.S. Application Data

(60) Provisional application No. 61/756,503, filed on Jan. 25, 2013.

(51) Int. Cl.
*A01N 25/04* (2006.01)
*A01N 43/90* (2006.01)
*A01N 53/00* (2006.01)

(52) U.S. Cl.
CPC ............. *A01N 25/04* (2013.01); *A01N 43/90* (2013.01); *A01N 53/00* (2013.01)

(58) Field of Classification Search
None
See application file for complete search history.

(56) References Cited

U.S. PATENT DOCUMENTS 8,053,393 B2   11/2011   Patel et al.
8,759,529 B2   6/2014    Goto et al.

FOREIGN PATENT DOCUMENTS

| CN | 101309588 | 11/2008 |
|----|-----------|---------|
| CN | 101621272 | 9/2010 |
| EP | 2223599   | 9/2010  |
| WO | WO 2012035015 | 3/2012 |
| WO | WO 2013135606 | 9/2013 |

OTHER PUBLICATIONS

International Preliminary Report on Patentability, issued in PCT/EP2014/051377, dated Jan. 26, 2015.
International Search Report< issued in PCT/EP2014/051377, dated Mar. 3, 2014.

*Primary Examiner* — Jennifer A Berrios
(74) *Attorney, Agent, or Firm* — Brinks Gilson & Lione

(57) ABSTRACT

The present invention relates to a method for producing an aqueous suspension concentrate formulation and novel suspension concentrate formulations of the compound of formula I. The method comprises the steps a) to d) as described hereinafter: a) providing an aqueous slurry of the compound of the formula I containing the compound of formula I in the form of coarse particles dispersed in a solution of the at least one surfactant in water; b) comminuting the coarse particles in the slurry of the compound of formula I to obtain an aqueous suspension of the compound of the formula I, wherein the particles of the compound of the formula I have an volume average particle size in the rage from 3 to 10 μm, as determined by light scattering; c) keeping the suspension of step b) at a temperature in the range of 20 to 95° C., d) subjecting the suspension of step c) to a further comminution to obtain an aqueous suspension of the compound of the formula I, wherein the particles of the compound of the formula I have an volume average particle size of below 3 μm, as determined by light scattering.

Formula I

18 Claims, No Drawings

METHOD FOR PRODUCING AQUEOUS SUSPENSION CONCENTRATE FORMULATIONS

This application is a National Stage application of International Application No. PCT/EP2014/051377, filed Jan. 24, 2014, which claims the benefit of U.S. Provisional Application No. 61/756,503, filed Jan. 25, 2013.

The present invention relates to a method for producing aqueous suspension concentrate formulations and novel suspension concentrate formulations of the compound of formula I.

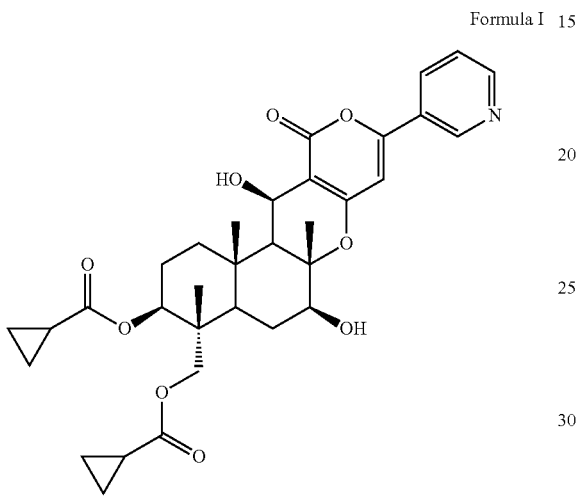

Formula I

The compound of formula I, hereinafter also termed pyripyropene derivative I, is known from EP 2223599 (compound no. 4) as exhibiting pesticidal activity against invertebrate pests, in particular against insects, and thus being useful for crop protection.

It is highly desirable to formulate a solid agriculturally active ingredient, such as a fungizide, herbicide or insecticide compound, as an aqueous suspension concentrate formulation, as these formulations contain no or only small amounts of organic volatiles. On the other hand, suspension concentrate formulations of solid organic active ingredients tend to be unstable against settling of the active ingredient due to particle growth or agglomeration of the active compound particles. Aqueous suspension concentrates are liquid aqueous formulations are usually prepared by suspending the solid active ingredient in an aqueous liquid containing a suitable surfactant for stabilizing the solid particles of the active ingredient and then comminuting the active ingredient particles down to the desired particle size, which is normally below 10 μm (volume average diameter as determined by light scattering).

EP 2223599 suggests various agrochemical formulations of the pyripyropene derivative I, including an aqueous suspension concentrate formulation, and suitable additives for such formulations. However, when trying to formulate the pyripyropene derivative I as an aqueous suspension concentrate one faces several difficulties, as the aqueous suspension concentrate formulation has only poor stability upon storage. In particular pronounced particle growth is observed, presumably due to the formation of agglomerates. Moreover, it is difficult to prepare an aqueous suspension concentrate of pyripyropene derivative I, as gelling may occur upon comminuting the active ingredient particles.

WO 2012/035015 shows that different hydrates forms of pyripyropene derivative I exist and hydrate formation may be one reason for the inherent instability of the aqueous suspension concentrate formulations of EP 2223599. WO 2012/035015 teaches that the stability problems can be overcome by providing a suspension concentrate formulation of the pyripyropene derivative I, which contains specific surfactant combination, i.e.

6 to 20% by weight, based on the total weight of the formulation, of an anionic polymeric surfactant having a plurality of $SO^{3-}$ groups, and 0.1 to 10% by weight, based on the total weight of the formulation, of a non-ionic surfactant, in particular a poly(ethyleneoxide-co-propyleneoxide) polymers having a HLB of at least 12.

It is believed that the specific surfactant system of WO 2012/035015 favours the formation of a specific hydrate form, namely form Y (also termed form A), which renders the formulation more stable. Form Y in an X-ray powder diffractogram at 25° C. and Cu-$K_\alpha$ radiation, shows at least three, frequently at least four, in particular at least 5 or all of the following reflexes, given as 2θ values: 9.7±0.2°, 10.3±0.2°, 11.3±0.2°, 14.0±0.2°, 15.5±0.2°, 16.4±0.2°, 17.6±0.2°. Nevertheless, the problem of gelling occurs, in particular, if the compound of formula I has a purity of 95% or higher, especially a purity of 97% or higher.

U.S. provisional patent application 61/609,428 (published as WO 2013/135606) discloses a method for producing an aqueous suspension concentrate formulation of a compound of formula I, which formulation contains the compound of formula I in the form of fine particles and which also contains at least one surfactant and water, which method comprises:

a) providing an aqueous slurry of coarse particles of the compound of the formula I, where the compound of the formula I is at least partially present in its crystalline form B, which, in an X-ray powder diffractogram at 25° C. and Cu-$K_\alpha$ radiation, shows at least three, preferably at least four, in particular at least 5 or at least 7 or at least 9 or all of the following reflexes, given as 2θ values: 8.0±0.2°, 9.5±0.2°, 10.7±0.2°, 11.0±0.2°, 11.2±0.2°, 11.7±0.2°, 14.2±0.2°, 15.6±0.2°, 16.5±0.2°, 17.7±0.2°, 21.5±0.2°;

b) comminuting the coarse particles in the slurry of the compound of formula I, which is at least partially present in its form B, in the presence of the at least one surfactant.

The inventors of the present invention found that the problems associated with the formulation of pyripyropene derivative I as an aqueous suspension concentrate can also be overcome by a further specific method of its preparation, which method comprises the steps a) to d) as described hereinafter:

a) providing an aqueous slurry of the compound of the formula I containing the compound of formula I in the form of coarse particles dispersed in a solution of at least one surfactant in water;

b) comminuting the coarse particles in the slurry of the compound of formula I to obtain an aqueous suspension of the compound of the formula I, wherein the particles of the compound of the formula I have an volume average particle size in the range from 3 to 10 μm, as determined by light scattering;

c) keeping the suspension of step b) at a temperature in the range of 20 to 95° C., d) subjecting the suspension of step c) to a further comminution to obtain an aqueous suspension of the compound of the formula I, wherein the particles of the compound of the formula I have an volume average particle size of below 3 μm, as determined by light scattering.

Therefore the present invention relates to a method for producing aqueous suspension concentrate formulations of the compound of formula I in the form of fine particles containing at least one surfactant and water, which method comprises subsequent steps a) to d) as described herein.

The method of the present invention allows the preparation of stable aqueous suspension concentrate formulations of the compound of formula I in a reliable and time efficient manner. Contrary to the method described in WO 2013/135606 no gelling occurs. Apart from that, the method is not limited to the use of a specific surfactant system for obtaining a stabile, Contrary to the method described in 61/609,428 (WO 2013/135606), no conversion of the compound of formula I into its form B is required, which renders the method of the present invention less time consuming.

In the first step a) of the method of the present invention, an aqueous slurry of coarse particles of the compound of the formula I is provided. The term "coarse particle" means that the particles are bigger than the particles usually contained in a suspension concentrate formulations, which means that the volume average diameter of the particles of pyripyropene derivative I generally exceeds 15 μm, and is in particular at least 20 μm or at least 25 μm and may range from 15 μm to 1000 μm, in particular from 20 μm to 500 μm or from 25 μm to 200 μm.

The average particle diameter as referred herein, is the volume average particle diameters d(0.5) or d(v, 0.5), i.e. 50 vol.-% of the particles have a diameter which is above the value cited and 50 vol.-% of the particles have a diameter which is below the value cited. Therefore, average particle diameters are also termed "volume median diameters". Such average particle diameters can be determined by dynamic light scattering (usually performed on diluted suspensions containing from 0.01 to 5% by weight of the active ingredient). A skilled person is familiar with these methods which are described e.g. in H. Wiese (D. Distler, Ed.), Aqueous Polymer Dispersions (Wassrige Polymerdispersionen), Wiley-VCH 1999, Chapter 4.2.1, p. 40ff, and the literature cited therein; H. Auweter, D. Horn, J. Colloid Interf. Sci. 105 (1985), p. 399; D. Lilge, D. Horn, Colloid Polym. Sci. 269 (1991), p. 704; and H. Wiese, D. Horn, J. Chem. Phys. 94 (1991), p. 6429.

The aqueous slurry can be simply provided by suspending a solid form of the compound of the formula I in water, which contains at least a portion of the surfactant contained in the formulation. As a starting material for the preparation of the slurry, any crystalline or amorphous form or mixtures of different crystalline forms or mixtures of amorphous forms or crystalline forms of the pyripyropene compound of formula I can be used for preparing the slurry. Usually the form of the pyripyropene compound of formula I, which is used for preparing the slurry is different from crystalline forms B and Y. However, these crystalline forms B and Y may also be used.

In a preferred embodiment of the invention, the slurry is prepared from a crystalline solvate of the compound of formula I. In particular the solvate is a crystalline solvate of the compound of formula I with a $C_1$-$C_4$-alkyl benzene, especially a solvate of the compound of formula I with toluene or ethylbenzene. These crystalline solvates of the compound of formula I can be prepared by crystallization of the compound of formula I from a solution of the compound of the formula I in a $C_1$-$C_4$-alkyl benzene containing solvent or solvent mixture, in particular from a solution of the compound of the formula I in a $C_1$-$C_4$-alkyl benzene, especially from a solution in toluene or ethylbenzene.

The purity of the pyripyropene derivative I used in the method of the present invention is of minor importance. The pyripyropene derivative I will normally have a purity sufficient for its intended use as a pesticide. The purity of the pyripyropene derivative I will be generally at least 90%, in particular at least 95% or at least 97%. Purity has to be understood as the relative amount of pyripyropene derivative I in the organic solid active ingredient suspended in the slurry, except for solvents, e.g. solvents contained in the solvate.

The concentration of the pyripyropene compound of formula I in the slurry is of minor importance. For practical reasons the concentration of the compound of formula I in the aqueous slurry is from 1 to 60% by weight, in particular from 2 to 50% by weight, especially from 3 to 40% by weight or from 5 to 30%, based on the total weight of the aqueous slurry.

According to the invention, the aqueous slurry which is subjected to the comminution of step b) contains at least one surfactant, which assists stabilization of the fine particles during and after comminution. The surfactant contained in the slurry may be present in the water, wherein the solid form of the pyripyropene derivative I is suspended, or it is added to the slurry at any time prior to step b). Preferably, the major amount of surfactant, in particular at least 50% by weight, especially at least 80 wt %, based on the total amount of surfactant contained in the final formulation, is added prior to step b), or all of the surfactant is added prior to step b). However, it may also be beneficial to add some of the surfactant, e.g. from 1 to 50% by weight, in particular from 2 to 20% by weight, based on the total amount of surfactant contained in the formulation, during or after step b). Preferably, the concentration of surfactant in the slurry during step a) is in the range from 0.5 to 25% by weight, in particular from 1 to 20% by weight, based on the total weight of the aqueous slurry.

Preferably, the slurry does not contain organic solvents, i.e. the concentration of organic solvent does not exceed 2% by weight, based on the total weight of the aqueous slurry.

Suitable surfactants are those, which are commonly used as a surfactant for the stabilization of an aqueous suspension concentrate formulation of a solid active ingredient. Suitable surfactants may by anionic or non-ionic.

It has been found advantageous, if the surfactant comprises at least one anionic surfactant. The concentration of anionic surfactant in the suspension during step b) will generally be in the range from 0.1 to 20% by weight, in particular from 0.5 to 15% by weight.

Suitable anionic surfactants are those, which have at least one acidic functional group, which is present in water at pH 7 in its anionic salt form. Suitable functional groups are $SO_3H$, which is present in water at pH 7 as $SO_3^-$, and $PO_3H_2$, which is present in water at pH 7 as $PO_3H^-$ or $PO_3^{2-}$.

Suitable anionic surfactants include anionic emulsifiers and anionic polymeric surfactants. In contrast to anionic emulsifiers, the anionic polymeric surfactants will generally have a molecular weight of above 800 Dalton (number average). Suitable anionic surfactants are alkali metal salts, alkaline earth metal salts and ammonium salts of aromatic sulfonic acids, such as benzene sulfonic acid, phenol sulfonic acid, $C_1$-$C_{20}$-alkylbenzene sulfonic acid, naphthalene or alkylnaphthalene sulfonic such as dibutylnaphthalene-sulfonic acid (Nekal® types, BASF, Germany), alkylsulfonates, alkylarylsulfonates, alkylsulfates, such as laurylether sulfates, fatty alcohol sulfates, such as sulfated lauryl alcohol, sulfated hexa-, hepta- and octadecanolates, sulfated polyethoxylates of fatty alcohols, sulfated polyethoxylates of $C_1$-$C_{20}$-alkylphenols and sulfated polyethoxylates of di- or tristyrylphenol and the anionic polymeric surfactant having a plurality of $SO_3^-$ groups as described hereinafter.

The term "polyethoxylates" means that the compound has a polyethylenoxide radical. In these polyethoxylates the amount of oxyethylene repeating units $CH_2CH_2O$ will usually be in the range from 2 to 100, especially from 4 to 80.

Preferably, the anionic surfactant is selected from anionic polymeric surfactant having a plurality of $SO_3^-$ groups, i.e. at least 2 in particular at least 3 $SO_3^-$ groups. Suitable anionic polymeric surfactants having a plurality of $SO_3^-$ groups include but are not limited to the salts, in particular the alkali metal salts, alkaline earth metal salts and ammonium salts, especially the sodium, calcium or ammonium salts of i. condensates of arylsulfonic acids, such as benzene sulfonic acid, phenol sulfonic acid, alkylbenzene sulfonic acid (e.g. toluene sulfonic acid), naphthalene or alkylnaphthalene sulfonic acid such as $C_1$-$C_{10}$-alkylnaphthalene sulfonic acid, with formaldehyde and optionally with urea and the salts thereof, e.g. the earth alkaline salts, alkaline salts or ammonium salts, especially the sodium, calcium or ammonium salts;
ii. lignosulfonates and the salts thereof, e.g. the earth alkaline salts, alkaline salts or ammonium salts, especially their sodium, calcium or ammonium salts; and
iii. homo- and co-polymers of ethylenically unsaturated sulfonic acids, such as 2-acrylamido-2-methylpropane sulfonic acid, 2-acryloxyethane sulfonic acid, 2-acryloxy-2-methylpropane sulfonic acid, styrenesulfonic acid or vinylsulfonic acid, optionally in the form of a copolymer with a monoethylenically unsaturated monomer, which is e.g. selected from $C_3$-$C_5$ monoethylenically unsaturated carboxylic acid monomers such as acrylic acid or methacrylic acid, $C_1$-$C_6$-alkylesters of $C_3$-$C_5$ monoethylenically unsaturated carboxylic acid monomers such as $C_1$-$C_6$ alkylacrylates and -methacrylates, $C_2$-$C_6$-hydroxyalkylesters of $C_3$-$C_5$ monoethylenically unsaturated carboxylic acid monomers such as $C_2$-$C_6$ hydroxyalkylacrylates and -methacrylates, vinylaromatic monomers such as styrene and $C_2$-$C_{12}$-monoolefines such as ethene, propene, 1-butene, isobutene, hexene, 2-ethylhexene, diisobutene (mixture of isobuten dimers), tripropene, tetrapropene, triisobutene etc. and the salts of these homo- and co-polymers, e.g. the earth alkaline salts, alkaline salts or ammonium salts, especially the sodium, calcium or ammonium salts Preferably, the anionic polymeric surfactant having a plurality of $SO_3^-$ groups is selected from the aforementioned salts of condensates of arylsulfonic acids mentioned as group i. In particular the anionic polymeric surfactant having a plurality of $SO_3^-$ groups is selected from the salts of naphthalene sulfonic acid formaldehyde condensates, salts of alkylnaphthalene sulfonic acid formaldehyde condensates and the salts of naphthalene sulfonic acid formaldehyde urea co-condensates. In a particular preferred embodiment, the anionic polymeric surfactant having a plurality of $SO^{3-}$ groups is an alkaline metal salts or earth alkaline metal salt of a reaction product (condensate) of naphthalene sulfonic acid and formaldehyde; particularly suitable examples are the Morwet® grades such as Morwet® D400, D425, D440, D450 or D500 (Akzo Nobel), the Tamol® NN grades of BASF SE, Surfaron® A 1530 N100 or Surfaron® A 1543 N100 (Synthron) and the Tersperse® grades such as Tersperse® 2001, 2020, 2100 or 2425 of Huntsman.

In a particular embodiment, the surfactant comprises at least one non-ionic surfactant in addition to the at least one anionic surfactant. If present, the concentration of non-ionic surfactant in the suspension in step a) as well as during step b) will generally be in the range from 0.1 to 20% by weight, in particular from 0.5 to 15% by weight. If present, the weight ratio of non-ionic surfactant to anionic surfactant may be in the range from 10:1 to 1:20, in particular from 5:1 to 1:10.

Suitable non-ionic surfactants are non-ionic emulsifiers having at least one poly($C_2$-$C_4$-alkylenoxide), e.g. polyethoxylates of alkylphenols such as polyoxyethylene octylphenyl ether, polyoxyethylene isooctylphenyl ether, polyoxyethylene nonylphenyl ether, polyoxyethylene tributylphenyl ether, polyoxyethylene tristyrylphenyl ether and polyoxyethylene distyrylphenyl ether, polyethoxylates of fatty alcohols such as polyethoxylates of lauryl alcohol, myristyl alcohol, palmityl alcohol or stearyl alcohol, polyethoxylated castor oil, sorbitol esters, and polymeric non-ionic surfactants having at least one poly($C_2$-$C_4$-alkylenoxide) moiety, which are hereinafter also termed as poly($C_2$-$C_4$-alkylenoxide) polymers. In contrast to non-ionic polymeric surfactants, the non-ionic emulsifiers will generally have a molecular weight of above 1500 Dalton (number average).

A poly($C_2$-$C_4$-alkylenoxide) moiety is an aliphatic polyether moiety, which is constructed of oxy-$C_2$-$C_4$-alkylene repeating units, such as oxyethylene repeating units ($CH_2CH_2O$), oxy-1,2-propylene repeating units [($CH(CH_3)CH_2O$) or ($CH_2CH(CH_3)O$), respectively], oxy-1,2-butylene, oxy-2,3-butylene, oxy-1,4-butylene or oxy-1,1-dimethyl-1,2-ethylene repeating units [($C(CH_3)_2CH_2O$) or ($CH_2CH(CH_3)_2O$), respectively].

Preferably, the non-ionic surfactant is selected from poly($C_2$-$C_4$-alkylenoxide)polymers. Examples of poly($C_2$-$C_4$-alkylenoxide)polymers are non-ionic copolymers of ethyleneoxide and $C_3$-$C_4$-alkylene oxide which oxyethylene repeating units and oxy-$C_3$-$C_4$-alkylene repeating units, in particular block-copolymers having at least one poly(ethylenoxide)moiety PEO and at least one aliphatic polyether moiety PAO derived from $C_3$-$C_4$-alkylene oxides, in particular polyoxyethylene-polyoxypropylene-blockcopolymers. Further examples of poly($C_2$-$C_4$-alkyleneoxide)polymers are non-ionic graft copolymers containing polyethylene oxide moiety PEO grafted on a non-ionic, hydrophilic polymeric backbone.

Amongst the poly($C_2$-$C_4$-alkyleneoxide) polymers particular preference is given to poly(ethyleneoxide-co-propyleneoxide)polymers, in particular to those poly(ethyleneoxide-co-propyleneoxide)polymers, wherein the ethyleneoxide and propyleneoxide repeating units are arranged blockwise. Amongst the poly($C_2$-$C_4$-alkyleneoxide)polymers particular preference is given to poly(ethyleneoxide-co-propyleneoxide)polymers having a HLB value (HLB=hydrophilic-lipophilic balance) of at least 12, preferably at least 14, in particular at least 15, e.g. from 12 to 20, preferably from 14 to 19, in particular from 15 to 19, in particular to those poly(ethyleneoxide-co-propyleneoxide) polymers, wherein the ethyleneoxide and propyleneoxide repeating units are arranged blockwise. The HLB value referred to herein is the HLB value according to Griffin (W. C. Griffin, J. Soc. Cosmet. Chem. 1, 311 (1950); 5, 249 (1954)—see also H. Mollet et al. "Formulation Technology", 1st ed. Wiley-VCH Verlags GmbH, Weinheim 2001, pages 70-73 and references cited therein). Preferred poly ($C_2$-$C_4$-alkyleneoxide)polymers have a number average molecular weight in the range from 1500 to 50000 Dalton, in particular in the range from 1700 to 25000 Dalton.

Particular preference is given to non-ionic surfactants which are selected from the group of non-ionic block-copolymers. These non-ionic block copolymers preferably comprise at least one poly(ethylene oxide) moiety PEO and at least one hydrophobic polyether moiety PAO. The PAO moiety usually comprises at least 3, preferably at least 5, in particular 10 to 100 repeating units (number average) which are derived from $C_3$-$C_4$ alkylene oxides, such as propylene oxide, 1,2-butylene oxide, cis- or trans-2,3-butylene oxide or isobutylene oxide. Preferably, the PAO moieties comprise at least 50% by weight, and more preferably at least 80% by weight of repeating units derived from propylene oxide. The PEO moieties usually comprise at least 3, preferably at least 5, and more preferably at least 10 repeating units derived from ethylene oxide (number average). The weight ratio of PEO moieties and PAO moieties (PEO:PAO) usually ranges from 1:10 to 10:1, preferably from 1:2 to 5:1, more preferably from 1:1 to 4:1 and in particular from 1.1:1 to 3:1. Those are preferred which have a number average molecular weight MN ranging from more than 1500 to 100000 Dalton, preferably from 1700 to 25000 Dalton, more preferably from 2000 to 20000 Dalton. In general, the PEO moieties and the PAO moieties make up at least 80% by weight, and preferably at least 90% by weight, e.g. 90 to 99.5% by weight, of the non-ionic block copolymer surfactants.

Suitable blockcopolymers are described e.g. in WO2006/002984, in particular those having the formulae P1 to P5 given therein. The non-ionic block copolymer surfactants herein are commercially available e.g. under the trade names Pluronic®, such as Pluronic® P 65, P84, P 103, P 105, P 123 and Pluronic® L 31, L 43, L 62, L 62 LF, L 64, L 81, L 92 and L 121, Pluraflo® such as Pluraflo® L 860, L1030 and L 1060; Pluriol® such as Pluriol® WSB-125, Tetronic®, such as Tetronic® 704, 709, 1104, 1304, 702, 1102, 1302, 701, 901, 1101, 1301 (BASF SE), Agrilan® AEC 167 and Agrilan® AEC 178 (Akcros Chemicals), Antarox® B/848 (Rhodia), Berol® 370 and Berol® 374 (Akzo Nobel Surface Chemistry), Dowfax® 50 C15, 63 N10, 63 N30, 64 N40 and 81 N10 (Dow Europe), Genapol® PF (Clariant), Monolan®, such as Monolan® PB, Monolan® PC, Monolan® PK (Akcros Chemicals), Panox® PE (Pan Asian Chemical Corporation), Symperonic®, such as Symperonic® PE/L, Symperonic® PE/F, Symperonic® PE/P, Symperonic® PE/T (ICI Surfactants), Tergitol® XD, Tergitol® XH and Tergitol® XJ (Union Carbide), Triton® CF-32 (Union Carbide), Teric PE Series (Huntsman) and Witconol®, such as Witconol® APEB, Witconol® NS 500 K and the like.

Likewise particular preference is given to poly(ethoxylate-co-propoxylates) of $C_1$-$C_{10}$ alkanols, having a number average molecular weight MN of from 1500 to 20000 Dalton Particularly preferred examples include Atlox® G 5000 (Akzo Nobel), Tergitol®XD, Pluronic® P105 and Pluriol® WSB-125 and the like.

Preferred non-ionic graft copolymers contain, in polymerised form, (i) methyl esters or hydroxyl-$C_2$-$C_3$-alkyl esters of $C_3$-$C_5$ monoethylenically unsaturated carboxylic acid monomers, such as methyl acrylate, methyl methacrylate, hydroxyethyl acrylate and hydroxyethyl methacrylate and (ii) polyethylenoxide groups which are attached either via ester linkages or ether linkages to the polymer backbone. In a preferred embodiment, the backbone of these graft copolymers contains, in polymerized form, methyl methacrylate and polyethylene oxide esters of methacrylic acid, a particularly suitable example being Atlox® 4913 (Akzo Nobel), and the like.

According to the invention, the aqueous slurry of the coarse particles of the pyripyropene derivative I will be subjected to a comminution of step b), where the coarse particles are disintegrated down to the desired particle size, i.e. to a volume average particle diameter in the range of 3 to 10 µm, in particular in the range of 3 to 5 µm. The time required to achieve the desired degree of comminution can be determined by routine experiments. Preferably the suspended particles after comminution will have a $d_{90}$-value which does not exceed 20 µm, in particular 10 µm, i.e. not more than 10 vol.-% of the particles have a diameter which is above and at least 90 vol.-% of the particles have a diameter which is below the $d_{90}$-value cited. Preferably the suspended particles after comminution will have a $d_{10}$-value which is not lower than 2 µm, in particular not lower than 2.5 µm, i.e. not more than 10 vol.-% of the particles have a diameter which is below and at least 10 vol.-% of the particles have a diameter which is above the $d_{10}$-value cited.

In order to perform step b), the slurry of the compound of formula I containing the surfactant or surfactant mixture are treated in a suitable device which is capable of achieving reduction of the particle size of the coarse particles. Thus, step b) may be carried out by any physical attrition method, such as grinding, crushing or milling, in particular by wet grinding or wet milling, including e.g. bead milling, hammer milling, pin milling, and the like. In a preferred embodiment of the invention, step b) is carried out by bead milling. In particular, bead sizes in the range of from 0.05 to 5 mm, more particularly from 0.2 to 2.5 mm, and most particularly from 0.5 to 1.5 mm have been found to be suitable. In general, bead loadings in the range of from 40 to 99%, particularly from 70 to 97%, and more particularly from 65 to 95% may be used.

Step b) is carried out in apparatus suitable for this purpose, in particular apparatus suitable for wet grinding or wet milling methods as necessitated by the presence of the solvent b. Such apparatus are generally known. Thus, step (ii) is preferably carried out in mills, such as ball mills or bead mills, agitator ball mills, circulating mills (agitator ball mills with pin grinding system), disk mills, annular chamber mills, double cone mills, triple roll mills, batch mills, colloid mills, and media mills, such as sand mills. To dissipate the heat energy introduced during the grinding process, the grinding chambers are preferably fitted with cooling systems. Particularly suitable is the ball mill Drais Superflow DCP SF 12 from DRAISWERKE, INC. 40 Whitney Road. Mahwah, N.J. 07430 USA, a Drais Perl Mill PMC from DRAISWERKE, INC., the circulating mill system ZETA from Netzsch-Feinmahltechnik GmbH, the disk mill from Netzsch Feinmahltechnik GmbH, Selb, Germany, the bead mill Eiger Mini 50 from Eiger Machinery, Inc., 888 East Belvidere Rd., Grayslake, Ill. 60030 USA and the bead mill DYNO-Mill KDL from WA Bachofen AG, Switzerland.

Although, the temperature during step b) is of minor importance, it has been found advantageous to perform step b) in a manner that the temperature of the suspension does not exceed 50° C. Generally, step b) is performed at a temperature above 0° C. In particular a temperature in the range of from 5° C. to 40° C. have been found to be suitable. As the comminution introduces energy into the suspension, temperature can be simply maintained in these ranges by cooling.

The pressure conditions during comminution are generally not critical; thus, for example, atmospheric pressure has been found to be suitable.

In step b) an aqueous suspension of the compound of formula I is obtained containing the surfactant contained in the aqueous slurry and wherein the particles size of the suspended compound I particles is in the above given range. The concentration of the compound of formula I in the aqueous suspension is generally from 1 to 60% by weight, in particular from 2 to 50% by weight, especially from 3 to 40% by weight or from 5 to 30% by weight, based on the total weight of the aqueous suspension.

The suspension obtained in step c) is then kept at a temperature in the range from 20 to 95° C., in particular from 25 to 90° C. or from 30 to 90° C., especially from 40 to 80° C. Step c) is also called aging step. Higher temperature may be possible using a pressurized equipment. Lower temperatures may also be possible but then the suspension must be kept at these temperatures for a longer time at the low temperature prior to performing step d). Generally the slurry is kept for a time period of 0.5 h to 120, in particular for a time period of 1 h to 48 h, especially for a time period of 1.5 h to 24 h. In particular, the slurry is kept for a period of 0.5 h to 120 h at a temperature in the range from 25 to 90° C. Especially, the slurry is kept at a temperature from 30 to 90° C. for a period of 1 h to 48 h, even more especially at a temperature from 40 to 80° C. for a period of 1.5 h to 24 h.

During aging moderate shear may be applied, e.g. by stirring or rocking. However, during step c) the particle size of the coarse particles should not be further reduced to an average diameter of below 3 μm, in order to avoid gelling of the final suspension concentrate formulation. Generally, it has been found to be advantageous to perform step c) by applying moderate shear, in particular by stirring the suspension.

According to the invention, the aqueous suspension of the pyripyropene derivative I after aging of step c) will be subjected to a further comminution of step d), where the particles are further comminuted down to a volume average particle size below 3 μm, preferably to a volume average particle diameter in the range of 0.5 to 2.5 μm, in particular in the range of 0.8 to 2 μmin. The time required to achieve the desired degree of comminution can be determined by routine experiments. Preferably the suspended particles after comminution will have a $d_{90}$-value which does not exceed 10 μm, in particular 4 μm, i.e. not more than 10 vol.-% of the particles have a diameter which is above and at least 90 vol.-% of the particles have a diameter which is below the $d_{90}$-value cited. Preferably the suspended particles after comminution of step d) will have a $d_{10}$-value which is not lower than 0.2 μm, in particular not lower than 0.5 μm, i.e. not more than 10 vol.-% of the particles have a diameter which is below and at least 10 vol.-% of the particles have a diameter which is above the $d_{10}$-value cited.

During the aging of step d) a conversion of the solid material of the compound of formula I into its form Y can be observed. Preferably, step d) is performed until at least 50%, in particular at least 70% of the compound of formula I is present in its crystalline form Y. Form Y can be identified by its X-ray powder diffractogram. The X-ray powder diffractogram of form Y at 25° C. and Cu-$K_\alpha$ radiation, shows at least three, in particular at least 5 or all of the following reflexes, given as 2θ values: 9.7±0.2°, 10.3±0.2°, 11.3±0.2°, 14.0±0.2°, 15.5±0.2°, 16.4±0.2°, 17.6±0.2°.

It may be possible to add further surfactant prior to or during comminution of step d). It may also be possible to add further water prior to or during comminution of step d). Preferably, the concentration of surfactant in the suspension during steps b) to d) is in the range from 0.5 to 25% by weight, in particular from 1 to 20% by weight, based on the total weight of the aqueous suspension. The concentration of the pyripyropene compound of formula I in the suspension prior to or during step d) is of minor importance. For practical reasons the concentration of the compound of formula I in the aqueous suspension prior or during step d) is from 1 to 60% by weight, in particular from 2 to 50% by weight, especially from 3 to 40% by weight or from 5 to 30% by weight, based on the total weight of the aqueous suspension.

Although, the temperature during step d) is of minor importance, it has been found advantageous to perform step d) in a manner that the temperature of the suspension does not exceed 50° C. Generally, step d) is performed at a temperature above 0° C. In particular a temperature in the range of from 5° C. to 40° C. has been found to be suitable. As the comminution introduces energy into the suspension, temperature can be simply maintained in these ranges by cooling.

Apart from that, step d) can be performed by analogy to step b) using the equipments for comminution described in the context of step b).

To the aqueous suspension obtained from step d), one or more further formulation additives, e.g. rheology modifiers (i.e. thickeners), preservatives, antifoam and/or antifreeze, may be added, optionally together with further water and/or surfactant, if required. The amount of additives will generally not exceed 5% by weight, in particular 2% by weight of the total weight of the final formulation.

Suitable thickeners are compounds which confer a pseudoplastic flow behavior to the formulation, i.e. high viscosity at rest and low viscosity in the agitated stage. Mention may be made, in this connection, for example, of commercial thickeners based on polysaccharides, such as Xanthan Gum® (Kelzan® from Kelco; Rhodopol® 23 from Rhone Poulenc or Veegum® from R.T. Vanderbilt), or phyllosilicates which may be hydrophobized, such as Attaclay® (from Engelhardt). Xanthan Gum® is a preferred thickener.

Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof.

Bactericides can be added to stabilize the compositions according to the invention against attack by microorganisms. Suitable bactericides are, for example, based on isothiazolones such as the compounds marketed under the trademarks Proxel® from Avecia (or Arch) or Acticide® RS from Thor Chemie and Kathon® MK from Rohm & Haas.

It may be beneficial to add at least a part, in particular at least 20%, e.g. from 20 to 80%, of the antifoam agents prior to comminution of step b) or prior to comminution of step d). For example, the concentration of antifoaming agent in the slurry subjected to step b) may be in the range from 0.01 to 1% by weight, in particular form 0.05 to 0.5% by weight. For example, the concentration of antifoaming agent in the final suspension concentrate formulation may be in the range from 0.02 to 2% by weight, in particular form 0.1 to 1% by weight. Preferably, thickeners are not added only after step d).

The obtained aqueous suspension concentrate formulations of the present invention generally contain:

a) 1 to 50% by weight, in particular from 2 to 40% by weight, especially from 3 to 30% by weight, based on the total weight of the formulation, of the compound of formula I;
b) 0.2 to 25% by weight, in particular 2 to 20% by weight, especially 3 to 15% by weight, based on the total weight of the formulation, of at least one surfactant as defined above;
d) 40 to 98.8% by weight, in particular 50 to 96% by weight, especially 60 to 94% by weight, based on the total weight of the formulation, by weight of water.

The obtained aqueous suspension concentrate formulations of the present invention in particular contain:
a) 1 to 30% by weight, in particular 2 to 25% by weight, especially 3 to 15% by weight, based on the total weight of the formulation, of the pesticide compound of formula I;
b) 0.1 to 20% by weight, in particular 1 to 15% by weight, especially 1.5 to 12% by weight, based on the total weight of the formulation, of at least one anionic surfactant as defined above, where the anionic surfactant preferably comprises at least one anionic polymeric surfactant having a plurality of $SO^{3-}$ groups or which is preferably selected from anionic polymeric surfactants having a plurality of $SO^{3-}$ groups;
c) 0.1 to 20% by weight, in particular from 1 to 15% by weight, especially 1.5 to 10% by weight, based on the total weight of the formulation, of at least one non-ionic surfactant, which preferably comprises at least one poly($C_2$-$C_4$-alkylenoxide)polymer or is in particular selected from poly($C_2$-$C_4$-alkylenoxide)polymers,
d) 40 to 98.8% by weight, in particular 50 to 96% by weight, especially 60 to 94% by weight, based on the total weight of the formulation, by weight of water.

As explained above, the pyripyropene derivative I is at least partially converted into its form Y during step c) or during subsequent comminution of step d). In particular, the pyripyropene derivative I is converted into its form Y to an extent of generally at least 50% by weight, in particular at least 70% by weight, especially at least 80% by weight, completely or almost completely (i.e. at least 90% by weight), based on the total amount of the pyripyropene derivative I present during step c). Thus, in the suspension obtained in step d) and thus in the suspension concentrate formulation obtained by the process of the present invention, the pyripyropene derivative I is at least partially present in its form Y, frequently to an extent of at least 50% by weight, in particular at least 70% by weight, especially at least 80% by weight, completely or almost completely (i.e. at least 90% by weight), based on the total amount of the pyripyropene derivative in the suspension concentrate formulation.

The obtained aqueous formulation shows increased storage stability, in particular neither significant increase in particle size of the suspended particles, e.g. due to unwanted Ostwald's ripening or agglomeration, nor gelling, i.e. a significant increase in viscosity, is observed upon storage. The formulations of the present invention can be easily diluted with water without separation of active ingredients or creaming to occur.

The formulations obtained by the process of the present invention can be used for controlling insects, arachnids or nematodes. Such a use generally comprises contacting an insect, acarid or nematode or their food supply, habitat, breeding grounds or their locus with the formulation or a dilution thereof in pesticidally effective amounts.

The formulations obtained by the process of the present invention can be applied in a conventional manner, e.g. in diluted form as an aqueous ready-to-use preparation. Such an aqueous ready-to-use preparation can be applied by spraying, in particular spraying of the leaves. Application can be carried out using spraying techniques known to the person skilled in the art, for example using water as carrier and amounts of spray liquor of about 100 to 1000 liters per hectare, for example from 300 to 400 liters per hectare.

The aqueous ready-to-use preparations are generally prepared by diluting the formulation with water, generally with at least 5 parts of water, preferably at least 10 parts of water, in particular at least 20 parts of water and more preferably at least 50 parts of water, e.g. from 10 to 10,000, in particular from 20 to 1,000 and more preferably from 50 to 250 parts of water per one part of the liquid formulation (all parts are given in parts by weight). Dilution will be usually achieved by pouring the liquid concentrate formulation into water. Usually, dilution is achieved with agitation, e.g. with stirring, to ensure a rapid mixing of the concentrate in water. However, agitation is generally not necessary. Though the temperature of mixing is not critical, mixing is usually performed at temperatures ranging from 0 to 100° C., in particular from 10 to 50° C. or at ambient temperature. The water used for mixing is usually tap water. However the water may already contain water soluble compounds which are used in plant protection, e.g. nutrificants, fertilizers or water soluble pesticides.

With regard to further details regarding the use of the aqueous suspension concentrate formulations obtained by the process of the invention reference is made to EP 2223599 and WO 2012/035015.

The following examples further illustrate the present invention:

Starting Materials:

Insecticide A: Compound of formula I in the form of a crystalline solvate with ethyl benzene having an a.i. content of >95% by weight.

Surfactant 1: Sodium salt of a naphthalene sulfonic acid formaldehyde condensate—Morwet® D425 (Akzo Nobel).

Surfactant 2: $C_1$-$C_3$-alkylether of poly-$C_2$-$C_3$-alkylene glycol (MN 2900)—Atlox® G5000 (Croda), HLB 17.

Antifoaming agent: Silicon based defoamer—Silicon SRE-PFL (Wacker).

Preservative: Isothiazolinone—Acticide MBS (Thor).

Thickener: Xanthan Gum.

Analytics:

Particle Size distributions were determined by using a Malvern Mastersizer 2000 by using a 0.1-1% dilution of the respective specimen in water.

Viscosity of the formulation was determined at 20° C. by using AR 2000ex Rheometer of TA instruments.

COMPARATIVE EXAMPLE 1—INSTABLE SUSPENSION CONCENTRATE

An aqueous suspension concentrate (SC A) having the following composition was prepared by the process outlined below: 9.37% by weight of Insecticide A, 9.4% by weight of surfactant 1, 3.0% by weight of surfactant 2, 0.2% by weight of xanthan gum, 0.4% by weight of antifoaming agent, 0.16% by weight preservative and water up to 100% by weight.

The formulation was prepared as follows:
(a) 10.52 parts by weight of Insecticide A, 10.11 parts by weight of surfactant 1, 3.22 parts by weight of surfactant 2, 0.2 parts by weight of antifoaming agent and 75.95 parts by weight of water were mixed in a vessel to obtain an aqueous slurry.
(b) The slurry was then ground in a bead mill with sufficient ball loading to ensure effective milling efficiency. The temperature of grinding head was controlled at 5° C. The milling was stopped when an average particle size of 1.5-2 µm (volume average) had been achieved (measured with Malvern Mastersizer 2000). To the thus obtained suspension the remaining antifoaming agent, the preservative and the thickener and water were added to with stirring to ensure homogeneous distribution of components. The amount of water was chosen that the final concentration of the pyripyropene derivative in the formulation was 9.37% by weight.

The obtained formulation was then kept at 22° C. for two days. During this time, the suspension concentrate formulation became a non-flowable gel, which could not be diluted any longer.

EXAMPLE 1—STABLE SUSPENSION CONCENTRATE

An aqueous suspension concentrate (SC A) having the following composition was prepared by the process outlined below: 9.37% by weight of Insecticide A, 9.4% by weight of surfactant 1, 3.0% by weight of surfactant 2, 0.2% by weight of xanthan gum, 0.4% by weight of antifoaming agent, 0.16% by weight preservative and water up to 100% by weight.

The formulation was prepared as follows:
(a) 10.52 parts by weight of Insecticide A, 10.11 parts by weight of surfactant 1, 3.22 parts by weight of surfactant 2, 0.2 parts by weight of antifoaming agent and 75.95 parts by weight of water were mixed in a vessel to obtain an aqueous slurry.
(b) The slurry was then ground in a bead mill with sufficient ball loading to ensure effective milling efficiency. The temperature of grinding head was controlled at 5° C. The milling was stopped when an average particle size of 4-5 µm (volume average) had been achieved (measured with Malvern Mastersizer 2000).
(c) The thus obtained suspension was kept for 3 h at 65° C. with stirring;
(d) The thus obtained suspension suspension was then ground in a bead mill as described for step (b). The milling was stopped when an average particle size of 1-2 µm (volume average) had been achieved (measured with Malvern Mastersizer 2000). The remaining antifoaming agent, the preservative and the thickener and water were added to with stirring to ensure homogeneous distribution of components.

The apparent viscosity of the fresh prepared formulation at 20° C. was 91.2 mPas (shear rate 100 s$^{-1}$).

The volume average particle size of the pesticide particles in the fresh prepared formulation was 1.51 µm ($d_{50}$ value), the $d_{90}$ value was 4.40 µm.

Samples of the thus obtained formulation were then kept under various storage conditions for 1 month (22° C., −20° C. and cycling temperatures between −10° C. and +10° C. every 48 h). All samples remained flowable and stable. All samples could be easily diluted with water.

EXAMPLES 2 TO 4 AND COMPARATIVE EXAMPLE 2

Aqueous suspension concentrate formulations having the composition given for example 1 were prepared by analogy to the method given for example 1 with different holding times in step (c). The obtained formulations were kept for 1 week at 22° C. Then the physical stability was assessed visually. The results are summarized in table 1:

TABLE 1

| Example | Time in step (c) [h] | Stability |
| --- | --- | --- |
| 2 | 2 | Flowable |
| 3 | 3 | Flowable |
| 4 | 4 | Flowable |
| C2* | 0 | Non-flowable gel |

*Comparative Example 2

We claim:
1. A method for producing an aqueous suspension concentrate formulation of a compound of formula I in the form of fine particles;

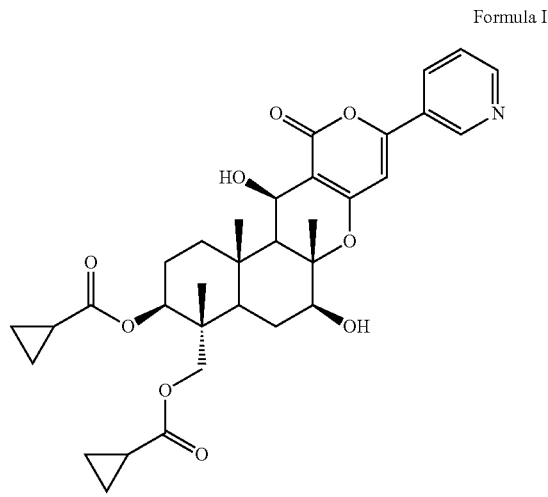

Formula I containing surfactants and water, wherein the surfactants comprises at least one anionic surfactant and at least one nonionic surfactant, wherein the method comprises:
a) providing an aqueous slurry of the compound of the formula I containing the compound of formula I in the form of coarse particles dispersed in a solution of the at least one surfactant in water;
b) comminuting the coarse particles in the slurry of the compound of formula I to obtain an aqueous suspension of the compound of the formula I, wherein the particles of the compound of the formula I have a volume average particle size in the range from 3 to 10 µm, as determined by light scattering, wherein step b is performed at a temperature in the range of above 0° C. to 50° C.;
c) subjecting the suspension obtained in step b to a temperature in the range of 20 to 95° C. for at least 0.5 hrs; and
d) subjecting the suspension of step c) to a comminution to obtain an aqueous suspension of the compound of the formula I, wherein the particles of the compound of the formula I have a volume average particle size of below 3 µm, as determined by light scattering.

2. The method of claim 1, wherein step b) is performed to achieve a volume average diameter of the particles in the range from 3 to 5 µm.

3. The method of claim 1, wherein comminution of the coarse particles in step b) is performed at a temperature from 5 to 40° C.

4. The method of claim 1, wherein the concentration of the compound of formula I in the aqueous suspension during step b) is from 5 to 50% by weight, based on the total weight of the suspension.

5. The method of claim 4, wherein the concentration of the compound of formula I in the aqueous suspension during step b) is from 8 to 40% by weight, based on the total weight of the suspension.

6. The method of claim 1, wherein at least 50% by wt. of the surfactants are present before performing step b).

7. The method of claim 1, wherein the concentration of the at least one surfactant in the aqueous suspension during step b) is from 1 to 30% by weight, based on the total weight of the aqueous suspension.

8. The method of claim 7, wherein the concentration of the at least one surfactant in the aqueous suspension during step b) is from 2 to 20% by weight, based on the total weight of the aqueous suspension.

9. The method of claim 1, wherein step c) is performed until at least 50% of the compound of formula I is present in its crystalline form Y, which, in an X-ray powder diffractogram at 25° C. and Cu-K$_\alpha$ radiation, shows at least three of the following reflexes, given as 2θ values: 9.7±0.2°, 10.3±0.2°, 11.3±0.2°, 14.0±0.2°, 15.5±0.2°, 16.4±0.2°, 17.6±0.2°.

10. The method of claim 1, wherein step c) is performed with stirring.

11. The method of claim 1, wherein step d) is performed at a temperature of not more than 50° C.

12. The method of claim 11, wherein step d) is performed at a temperature from 5 to 40° C.

13. The method of claim 1, wherein the compound of the formula I used in step a) is in the form of a crystalline solvate of the compound of formula I with a $C_1$-$C_4$-alkyl benzene.

14. The method of claim 1, wherein the anionic surfactant comprises at least one anionic polymeric surfactant having a plurality of $SO_3^-$ groups.

15. The method of claim 14, wherein the anionic polymeric surfactant having a plurality of $SO_3^-$ groups is selected from the group consisting of salts of naphthalene sulfonic acid formaldehyde condensates, salts of alkylnaphthalene sulfonic acid formaldehyde condensates and the salts of naphthalene sulfonic acid formaldehyde urea co-condensates.

16. The method of claim 1, wherein the non-ionic surfactant is selected from poly($C_2$-$C_4$)alkylenoxide polymers.

17. The method of claim 16, wherein the non-ionic surfactant is selected from poly(ethyleneoxide-co-propyleneoxide) polymers having a HLB of at least 12.

18. The method of claim 1, wherein the aqueous suspension concentrate formulation contains
a) 1 to 30 wt %, based on the total weight of the formulation, of the pesticide compound of formula I;
b1) 0.1 to 20 wt %, based on the total weight of the formulation, of at least one anionic surfactant,
b2) 0.1 to 20 wt %, based on the total weight of the formulation, of at least one non-ionic surfactant,
c) 40 to 98.8 wt %, based on the total weight of the formulation, by weight of water.

* * * * *